United States Patent
Ishii et al.

(10) Patent No.: US 6,232,258 B1
(45) Date of Patent: *May 15, 2001

(54) OXYGENATION CATALYST AND PROCESS FOR PRODUCING A KETONE USING THE SAME

(75) Inventors: Yasutaka Ishii, 19-21, Besshohonmachi, Takatsuki-shi, Osaka 569-1112; Tatsuya Nakano, Himeji, both of (JP)

(73) Assignees: Daicel Chemical Industries, Ltd.; Yasutaka Ishii, both of Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/072,354

(22) Filed: May 5, 1998

(30) Foreign Application Priority Data

May 13, 1997 (JP) ..................................... 9-122527

(51) Int. Cl.[7] .................................... B01J 31/02
(52) U.S. Cl. .......................... 502/155; 548/475; 568/357; 568/818
(58) Field of Search .................. 568/357, 571, 568/382, 383, 399, 910, 818, 910.5, 915; 502/155, 161, 209, 219, 220, 221, 222, 223; 548/475

(56) References Cited

U.S. PATENT DOCUMENTS 5,030,739   7/1991   Foricher et al. ..................... 552/542

FOREIGN PATENT DOCUMENTS

| 0198351A2 | 10/1986 | (EP) . |
| 0824962A1 | 2/1998 | (EP) . |
| 0858835A1 | 8/1998 | (EP) . |
| 8-038909A | 2/1996 | (JP) . |

OTHER PUBLICATIONS

Ishii et al, Journal of Organic Chemistry, vol. 61, pp. 4520–4526, 1996.*
English translation of "Lecture Draft II (1994) of 67th Spring Annual Meeting Chemical Society of Japan".
Tetrahedron, 24, 5369 (1968).
Tetrahedron, 24, 5361 (1968).

* cited by examiner

Primary Examiner—Sreeni Padmanabhan
(74) Attorney, Agent, or Firm—Birch, Stewart, Kolasch & Birch, LLP

(57) ABSTRACT

A substrate is contacted with oxygen in the presence of the imide compound shown by the following formula (1) (N-hydroxyphthalimide) and a strong acid, or the imide compound, the strong acid and a co-catalyst (e.g., a transition metal compound) to oxygenate the substrate with high conversion and selectivity:

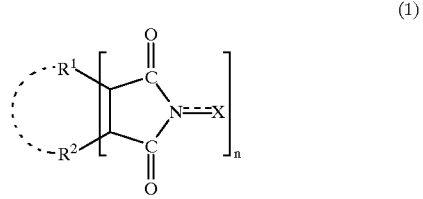

wherein $R^1$ and $R^2$ represent a substituent such as a hydrogen atom or a halogen atom, an alkyl group, an aryl group or a cycloalkyl group, or $R^1$ and $R^2$ may bond together to form a double bond or an aromatic or nonaromatic ring, X is O or OH, and n is 1 to 3.

The substrate comprises, for example, at least one compound selected from (a) a compound having a methyl group or a methylene group at an adjacent site of an unsaturated bond, (b) a homo- or hetero cyclic compound having a methylene group, (c) a compound having a methine carbon atom, (d) a compound having a methyl group or a methylene group at an adjacent site of an aromatic ring and (e) a compound having a methyl group or a methylene group at an adjacent site of a carbonyl group.

16 Claims, No Drawings

OXYGENATION CATALYST AND PROCESS FOR PRODUCING A KETONE USING THE SAME

FIELD OF THE INVENTION

This invention relates to a catalyst useful for efficiently oxygenating (oxidizing) a substrate with oxygen and an oxygenation process (an oxo-producing process) using the catalyst, and a process for producing a ketone (e.g., a monoketone, a polyketone, a hydroxyketone).

BACKGROUND OF THE INVENTION

An adamantanol derivative compound is a useful material as an commercial material. Specifically, a ketone among the adamantanol derivative compound is chemically used with comparative ease as a novel material or a material for medicines or agricultural chemicals, and commercial values thereof are increasing.

As a laboratory-level process for producing adamantanone, some technical examples using a three-step reaction are reported. The reaction comprises cationizing a separately prepared tertiary adamantanol, generating a secondary adamantanol with maintaining an equilibrium via 1,2-sigmatropy and converting it to an irreversible ketone body in a further continuous oxidation.

Schlatmann, for example, has reported that 2-adamantanone can be obtained in 72% yield by heating to maintain 1-adamantanol in concentrated sulfuric acid for 12 hours at 30° C. [Tetrahedronn, 24, 5361 (1968)].

Further, Geluk has reported that 2-adamantanol can be obtained in 50% yield from adamantane and in 70% yield from 1-damantanol, respectively, by heating to maintain them in 120-fold eqiv. concentrated sulfuric acid for 5 hours at 70° C. [Tetrahedronn, 24, 5369 (1968)].

These producing process, however, is not commercially suitable process because of using a large quantity of concentrated sulfuric acid. Moreover, the reaction is conducted under severe condition. Further, it is reported in these literatures that a slight deterioration of the condition of super strong acid insures a decrease of the yield of the ketone body, thus controlling the acidic condition is highly difficult. On the other hand, any process for producing a commercially useful hydroxyketone, polyketone or the like has not been reported.

Incidentally, a compound substituted by a hydroxyl group at a tertiary carbon atom of the site connecting adjacent rings each other, is useful as a physiologically active substance and has high utility values as an antiviral drug (agent), an antibacterial drug (agent), a plant hormone, and so forth. A compound bound by a functional group at a carbon atom of the connecting site of the rings, is broadly utilized as a raw material of various perfumes, a fragrant compound. Thus, a tertiary alcohol body having a hydroxyl group at the connecting site of rings, is an important compound. Therefore, producing a hydroxyketone body, which is a tertiary alcohol body and ketone body having a hydroxyl group at the connecting site of rings, is exceedingly important.

Japanese Patent Application Laid-open No. 38909/1996 (JP-A-8-38909) proposes a process for generating adipic acid by oxidizing cyclohexanone or cyclohexanol with molecular oxygen in the presence of an oxidation catalyst comprising an imide compound. A process for generating isocoumarin by oxidizing isochroman with molecular oxygen in the presence of the oxidation catalyst comprising the imide compound is also proposed.

On the page 762 of the "Lecture Draft II" (1994) of 67th Spring Annual Meeting of Chemical Society of Japan, it is reported that oxidation of adamantane with oxygen by using N-hydroxyphthalimide provides a corresponding alcohol or ketone. However, producing a ketone body or a hydroxyketone body, effectively and efficiently, with controlling a generation of a polyol body of a polycyclic hydrocarbon such as adamantane, is difficult. Specifically, it is difficult to give the ketone body and the hydroxyketone body with high conversion and selectivity.

SUMMARY OF THE INVENTION

It is, therefore, an object of the present invention to provide a catalyst which insures efficient oxygenation of a substrate with oxygen and a oxygenation process using the catalyst.

It is another object of the invention to provide a catalyst which can oxygenate a substrate with oxygen even in a mild or moderate condition and a oxygenation process using the catalyst.

A further object of the invention is to provide a catalyst which can provide a ketone with high conversion and selectivity by using oxygen and a oxygenation process using the catalyst.

It is yet another object of the invention to provide a process for producing a ketone, efficiently, in a simple operation and less steps.

The present inventors did much investigation to accomplish the above objects, and as a result, found that a reaction of a substrate with oxygen in the presence of a catalyst comprising a specific imide compound and a strong acid, insures efficient oxygenation of the substrate. The present invention has been accomplished based on the above findings.

Thus, a catalyst of the present invention, which is used for contacting a substrate with oxygen to oxygenate (oxidize) the substrate, comprises comprising an imide compound shown by the following formula (I),

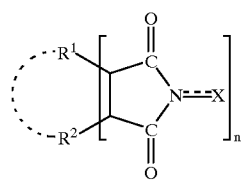

(1)

wherein $R^1$ and $R^2$ respectively represent a hydrogen atom, a halogen atom, an alkyl group, an aryl group, a cycloalkyl group, a hydroxyl group, an alkoxy group, a carboxyl group, an alkoxycarbonyl group, or an acyl group; or $R^1$ and $R^2$ may bond together to form a double bond, or an aromatic or non-aromatic ring; X represents an oxygen atom or a hydroxyl group; and n denotes an integer of 1 to 3,
and a strong acid. A pKa value of the strong acid at 25° C. is in the range of about −15 to 2.

The catalyst may comprise the imide compound shown by the formula (1), the strong acid and a co-catalyst. As such a co-catalyst, for instance, a compound containing at least one element selected from the group consisting of, for example, Group 2A elements of the Periodic Table of Elements, a transition metal element and Group 3B elements of the Periodic Table of Elements may be employed.

According to the present invention, a substrate is converted to a ketone by contacting the substrate with oxygen in the presence of the catalyst. The substrate comprises, for instance, (a) a compound having a methyl group or a methylene group at an adjacent site of an unsaturated bond, (b) a homo- or heterocyclic compound having a methylene group, (c) a compound having a methine carbon atom, (d) a compound having a methyl group or a methylene group at an adjacent site of an aromatic ring and (e) a compound having a methyl group or a methylene group at an adjacent site of a carbonyl group.

The present invention also comprises a process for producing a ketone corresponding to a substrate by using the oxygenation process.

DETAILED DESCRIPTION OF THE INVENTION

[Imide Compound]

In the imide compound shown by the formula (1), the halogen atom, as the substituents $R^1$ and $R^2$, includes iodine, bromine, chlorine and fluorine atoms. The alkyl group includes, for example, methyl, ethyl, propyl, isopropyl, butyl, isobutyl, sec-butyl, t-butyl, pentyl, hexyl, heptyl, octyl, decyl, or other straight chain or branched chain alkyl groups each having about 1 to 10 carbon atoms. An illustrative preferred alkyl group includes alkyl groups having about 1 to 6 carbon atoms, in particular lower alkyl groups having about 1 to 4 carbon atoms.

As the aryl group, there may be mentioned, for instance, a phenyl group and a naphthyl group. Examples of the cycloalkyl group include cyclopentyl, cyclohexyl, and cyclooctyl groups.

The alkoxy group includes, for example, methoxy, ethoxy, propoxy, isopropoxy, butoxy, isobutoxy, t-butoxy, pentyloxy, hexyloxy, and other alkoxy groups each having about 1 to 10 carbon atoms. Among them, alkoxy groups having about 1 to 6 carbon atoms, in particular lower alkoxy groups having about 1 to 4 carbon atoms are preferable. Examples of the alkoxycarbonyl group include methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl, and other alkoxycarbonyl groups each having about 1 to 10 carbon atoms in the alkoxy moiety. A preferred alkoxycarbonyl group includes those each having about 1 to 6 carbon atoms in the alkoxy moiety, among which lower alkoxycarbonyl groups each having about 1 to 4 carbon atoms in the alkoxy moiety are typically desirable.

The acyl group includes, for instance, formyl, acetyl, propionyl, butyryl, isobutyryl, valeryl, iso-valeryl, pivaloyl, and other acyl groups each having about 1 to 6 carbon atoms.

The substituents $R^1$ and $R^2$ may be either the same or different from each other. In the formula (1), $R^1$ and $R^2$ may bond together to form a double bond, or an aromatic or non-aromatic ring. A preferred aromatic or non-aromatic ring may be a ring having about 5 to 12 members, in particular about 6 to 10 members. Such a ring may be a heterocyclic ring or a condensed heterocyclic ring, and it may practically be a hydrocarbon ring. As such a ring, there may be mentioned, for instance, non-aromatic alicyclic rings (e.g., cyclohexane ring and other cycloalkane rings which may have a substituent, cyclohexene ring and other optionally substituted cycloalkene rings), non-aromatic bridged (cross-linked) rings (e.g., 5-norbornene ring and other optionally substituted bridged hydrocarbon rings), benzene ring, naphthalene ring and other optionally substituted aromatic rings. The ring may practically comprise an aromatic ring.

A preferred imide compound includes compounds shown by the following formula,

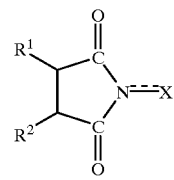

(1a)

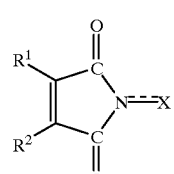

(1b)

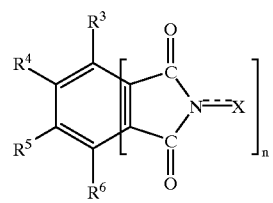

(1c)

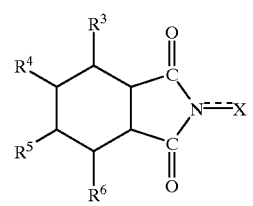

(1d)

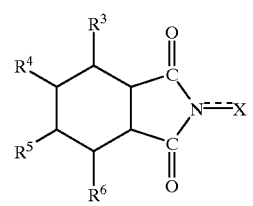

(1e)

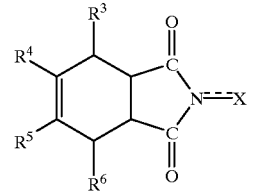

(1f)

wherein $R^3$, $R^4$, $R^5$ and $R^6$ independently represent a hydrogen atom, an alkyl group, a hydroxyl group, an alkoxy group, a carboxyl group, an alkoxycarbonyl group, an acyl group, a nitro group, a cyano group, an amino group or a halogen atom; and $R^1$, $R^2$ and n have the same meanings as defined above.

In the substituents $R^3$, $R^4$, $R^5$ and $R^6$, the alkyl group includes alkyl groups similar to those exemplified above, in particular alkyl groups each having about 1 to 6 carbon atoms. The alkoxy group includes the same alkoxy groups as mentioned above, in particular lower alkoxy groups each having about 1 to 4 carbon atoms. Examples of the alkoxycarbonyl group include the same alkoxycarbonyl groups as exemplified above, in especial lower alkoxycarbonyl groups each having about 1 to 4 carbon atoms in the alkoxy moiety. As the acyl group, there may be mentioned the similar acyl groups to those mentioned above, in particular acyl groups each having about 1 to 6 carbon atoms. Examples of the halogen atom include fluorine, chlorine and bromine atoms. The substituents $R^3$, $R^4$, $R^5$ and $R^6$ may practically be hydrogen atoms, lower alkyl groups each having 1 to 4 carbon atoms, carboxyl groups, nitro groups or halogen atoms, respectively.

The symbol X in the formula (1) denotes an oxygen atom or a hydroxyl group. Further, n usually denotes about 1 to 3, preferably 1 or 2. The imide compound shown by the formula (1) may be used singly or in combination in the carboxylation reaction.

Examples of the acid anhydride corresponding to the imide compound of the formula (1) includes a saturated or unsaturated aliphatic polycarboxylic acid anhydride, such as succinic anhydride and maleic anhydride; a saturated or unsaturated nonaromatic cyclic polycarboxylic acid anhydride (an alicyclic polycarboxylic acid anhydride) such as tetrahydrophthalic anhydride, hexahydrophthalic anhydride (1,2-cyclohexanedicarboxylic acid anhydride) and 1,2,3,4-cyclohexanetetracarboxylic acid 1,2-anhydride; a bridged cyclic polycarboxylic acid anhydride (an alicyclic polycarboxylic acid anhydride) such as hetic anhydride and himic anhydride; an aromatic polycarboxylic anhydride such as phthalic anhydride, tetrabromophthalic anhydride, tetrachlorophthalic anhydride, nitrophthalic anhydride, trimellitic anhydride, methylcyclohexenetricarboxylic anhydride, pyromellitic anhydride, mellitic anhydride and 1,8;4,5-naphthalenetetracarboxylic dianhydride.

Examples of a preferred imide compound include an imide compound derived from such as an aliphatic polycarboxylic acid anhydride (e.g., N-hydroxysuccinimide, N-hydroxymaleimide), an imide compound derived from an alicyclic polycarboxylic acid anhydride or aromatic poly carboxylic anhydride (e.g., N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxyhetimide, N-hydroxyhimimide, N-hydroxytrimellitimide, N,N'-dihydroxypyromellitimide, N,N'-dihydroxynaphthalenetetracarboximide). A specifically preferable imide compound includes an N-hydroxyimide compound derived from an alicyclic polycarboxylic anhydride, in particular from an aromatic polycarboxylic anhydride, such as N-hydroxyphthalimide.

The imide compound may be prepared by a conventional imidation process (a process for the formation of an imide), such as a process that comprises the steps of allowing a corresponding acid anhydride to react with hydroxylamine NH2OH for ring-opening of an acid anhydride group, and closing the ring to form an imide.

The amount used of the imide compound shown by the general formula (1) may be selected from the wide range such as about 0.001 mole (0.1 mole %) to 1 mole (100 mole %), preferably about 0.001 mole (0.1 mole %) to 0.5 mole (50 mole %), more preferably about 0.01 to 0.30 mole, and practically about 0.01 to 0.25 mole.

[Strong Acid]

Species of the strong acid are not particularly limited as far as the pKa values thereof at 251C are about 2 or less, for example. The pKa value of the strong acid is in the range of about −15 to 2, preferably, more preferably about −10 to 2. Preferred strong acid is an inorganic acid. Examples of available strong acid include a hydrogen halide (e.g., hydrogen bromide, hydrogen chloride, hydrogen iodide), a hydrohalogenic acid (e.g., hydrofluoric acid, bromic acid, hydrochloric acid, hydroiodic acid), a hydroxy acid such as sulfuric acid, nitric acid, phosphoric acid, a metallic acid (e.g., chromic acid),and a halogen acid (e.g., chloric acid $HClO_3$, iodic acid $HIO_3$), a super strong acid, a polyacid (e.g., a heteropolyacid or a isopolyacid). The super strong acid has a Hammett's acidity function $H_0$ of less than −11.93. These inorganic acids may be employed singly or in combination.

The super strong acid comprises, for instance, Brbnsted acids such as hydrogen halide (e.g., hydrogen fluoride HF) and a compound in which a hydrogen atom of the Bronsted acids such as sulfuric acid is substituted with an electron attractive atom or group, a mixture of the Bronsted acids and a Lewis acid (e.g., antimony pentafluoride $SbF_5$, sulfur trioxide $SO_3$). Examples of the super strong acid include, $ClSO_3H$, $H_2SO_4$—$SO_3$, $FSO_3H$, $FSO_3H$—$SO_3$, $SbF_5$, $FSO_3H$—$SbF_5$, HF—$SbF_5$, HF—$NbF_5$, HF—$TaF_5$, $FSO_3H$—$TaF_5$ and $SbF_5$—$CF_3SO_3H$.

In most cases, the polyacid comprises at least one member selected from Group 5 elements and Group 6 elements of the Periodic Table of Elements, such as V (vanadic acid), Mo (molybdic acid) or W (tungstic acid), typically speaking. There is no particular limit as to the central atom, and it may be any of, for instance, Be, B, Al, Si, Ge, Sn, Ti, Zr, Th, N, P, As, Sb, V, Nb, Ta, Cr, Mo, W, S, Se, Te, Mn, I, Fe, Co, Ni, Rh, Os, Ir, Pt or Cu. As illustrative examples of the heteropolyacid, there may be mentioned cobaltmolybdic acid, cobalttungstic acid, molybdenumtungstic acid, manganesemolybdic acid, manganesetungstic acid, manganesemolybdenumtungstic acid, vanadomolybdophosphoric acid, manganesevanadiummolybdic acid, manganesevanadomolybdophosphoric acid, vanadiummolybdic acid, vanadiumtungstic acid, silicomolybdic acid, silicotungstic acid, phosphomolybdic acid, phosphotungstic acid, phosphovanadomolybdic acid, phosphovanadotungstic acid. These polyacids are usually employed as free acids.

Examples of preferred strong acids include a hydrogen halide (e.g., hydrogen fluoride, hydrogen chloride, hydrogen iodide), a hydrohalogenic acid (e.g., hydrofluoric acid, hydrobromic acid, hydrochloric acid, hydroiodic acid), and sulfuric acid.

The amount of the strong acid may be selected suitably from the range which does not inhibit the oxidation of the substrate. The range is, for instance, about 0.00001 to 1 mole (0.001 to 100 mole %), preferably about 0.0005 to 0.7 mole (0.05 to 70mole %), more preferably about 0.005 to 0.5 mole (0.1 to 50 mole %) relative to 1 mole of the substrate. Excess amount of the strong acid tends to inhibit the oxidation reaction itself. Further, in the case of using a heteropolyacid as a strong acid, the amount used thereof is about 0.004 to 0.7 mole, preferably about 0.004 to 0.5 mole, most preferably about 0.005 to 0.1 mole relative to 1 mole of the substrate.

The amount used of the strong acid relative to the imide compound is, for example, about 0.01 to 1 mole, preferably about 0.03 to 0.7 mole, more preferably about 0.05 to 0.5 mole relative to the 1 mole of the imide compound.

In the case of using a solid catalyst as the catalyst, a solid acid may be employed wherein the acidity function (-Ho) of the solid acid is about 1 to 25, preferably about 3 to 25, more preferably about 4 to 20. An available solid acid as the strong acid comprises a metal oxide such as vanadium oxide, a sulfate such as copper sulfate, a chloride such as alminium chloride and the like.

[Co-catalyst]

The catalyst may be comprised the imide compound shown by the formula (1), the strong acid and a co-catalyst. The co-catalyst includes or comprises metal compounds such as a compound comprising or containing a Group 2A element of the Periodic Table of Elements (e.g., magnesium, calcium, strontium, barium), a transition metal compound, or compounds containing a Group 3B element (e.g., boron B, aluminium Al) of the Periodic Table of Elements. These co-catalysts may be employed independently or in combination.

As the elements of the transition metal, there may be mentioned, for instance, Group 3A elements of the Periodic Table of Elements (e.g., scandium Sc, yttrium Y, and lanthanum La, cerium Ce, samarium Sm and other lanthanoid elements, actinium Ac and other actinoid elements), Group 4A elements of the Periodic Table of Elements (e.g., titanium Ti, zirconium Zr, hafnium Hf), Group 5A elements (e.g., vanadium V, niobium Nb, tantalum Ta), Group 6A elements (e.g., chromium Cr, molybdenum Mo, tungsten W), Group 7A elements (e.g., manganese Mn, technetium Tc, rhenium Re), Group 8 elements (e.g., iron Fe, ruthenium Ru, osmium Os, cobalt Co, rhodium Rh, iridium Ir, nickel Ni, palladium Pd, platinum Pt), Group 1B elements (e.g., copper Cu, silver Ag, gold Au) and Group 2B elements of the Periodic Table of Elements (e.g., zinc Zn, cadmium Cd).

A preferred element constituting the co-catalyst includes elements of the transition metals (e.g., lanthanoid elements such as Ce, Group 3A elements of the Periodic Table of Elements such as actinoid elements, Group 4A elements such as Ti and Zr, Group 5A elements such as V and Nb, Group 6A elements such as Cr, Mo and W, Group 7A elements such as Mn, Tc and Re, Group 8 elements such as Fe, Ru, Co, Rh and Ni and Group 1B elements such as Cu) and Group 3B elements of the Periodic Table of Elements such as B. The oxidation number of the metal elements constituting the co-catalyst is not particularly limited, and may be, for example, 0, +2, +3, +4, +5 and +6, depending on the species of the elements. A divalent transition metal compound (e.g., a divalent cobalt compound, a divalent manganese compound) and a trivalent transition metal compound (e.g., a trivalent vanadium compound, a trivalent molybdenum compound) are practically employed.

The co-catalyst may be a simple substance or hydroxide of a metal, and may usualy be an oxide of a metal (a double oxide or an oxygen acid salt) comprising the element, an organic acid salt, an inorganic acid salt, a halide, a coordinate compound (a complex) comprising the metal element, or a polyacid (a heteropolyacid or an isopolyacid) salt.

As the boron compound, there may be mentioned, for example, a boron hydride (e.g., borane, diborane, tetraborane, pentaborane, decaborane), aboric acid (e.g., orthoboric acid, metaboric acid, tetraboric acid), a borate (e.g., anickel borate, magnesium borate, manganese borate), $B_2O_3$, and other boron oxides, borazane, borazene, borazine, boron amide, boron imide, and other nitrogen-containing boron compounds, $BF_3$, $BCl_3$, tetrafluoroborate, and other halides, esters of boric acid (e.g., methyl borate, phenyl borate). A preferred boron compound includes boron hydrides, orthoboric acid, and other boric acids or salts thereof, among which a boric acid can preferably be employed.

The hydroxide includes $Mn(OH)_2$, $MnO(OH)$, $Fe(OH)_2$ and $Fe(OH)_3$, typically speaking. Examples of the metallic oxide include $Sm_2O_3$, $TiO_2$, $ZrO_2$, $V_2O_3$, $V_2O_5$, $CrO$, $Cr_2O_3$, $MoO_3$, $MnO$, $Mn_3O_4$, $Mn_2O_3$, $MnO_2$, $Mn_2O_7$, $FeO$, $Fe_2O_3$, $Fe_3O_4$, $RuO_2$, $RuO_4$, $CoO$, $CoO_2$, $Co_2O_3$, $RhO_2$, $Rh_2O_3$, $Cu_2O_3$ and so forth. As examples of the double oxide or oxygen acid salt, there may be mentioned $MnAl_2O_4$, $MnTiO_3$, $LaMnO_3$, $K_2Mn_2O_5$, $CaO.MnO_2$ (x=0.5, 1, 2, 3, 5), manganese salts [e.g., $Na_3MnO_4$, $Ba[MnO_4]_2$ and other manganates (V), $K_2MnO_4$, $Na_2MnO_4$, $BaMnO_4$, and other manganates (VI), $KMnO_4$, $NaMnO_4$, $LiMnO_4$, $NH_4MnO_4$, $CsMnO_4$, $AgMnO_4$, $Ca(MnO_4)_2$, $Zn(MnO_4)_2$, $Ba(MnO_4)_2$, $Mg(MnO_4)_2$, $Cd(MnO_4)_2$ and other permanganates] and the like.

As the organic acid salts, there may be exemplified as cobalt acetate, manganese acetate, cobalt propionate, manganese propionate, cobalt naphthenate, manganese naphthenate, cobalt stearate, manganese stearate, and other salts with a $C_{2-20}$ fatty acid, manganese thiocyanate, and corresponding salts of Ce, Ti, Zr, V, Cr, Mo, Fe, Ru, Ni, Pd, Cu and Zn. The inorganic acid salt includes, for instance, cobalt nitrate, iron nitrate, manganese nitrate, nickel nitrate, copper nitrate, and other nitrates, and sulfates, phosphates, carbonates and perchlorates each corresponding to these nitrates (e.g., cobalt sulfate, iron sulfate, manganese sulfate, cobalt phosphate, iron phosphate, manganese phosphate, an iron carbonate, a manganese carbonate, iron perchlorate). As the halides, there may be mentioned, for instance, $SmCl_3$, $SmCl_2$, $TiCl_2$, $ZrCl_2$, $ZrOCl_2$, $VCl_3$, $VOCl_2$, $MnCl_2$, $MnCl_3$, $FeCl_2$, $FeCl_3$ $RuCl_3$, $CoCl_2$, $RhCl_2$, $RhCl_3$, $NiCl_2$, $PdCl_2$, $PtCl_2$, $CuCl$, $CuCl_2$, and other chlorides, or fluorides, bromides or iodides each corresponding to these chlorides (e.g., $MnF_2$, $MnBr_2$, $MnF_3$, $FeF_2$, $FeF_3$, $FeBr_2$, $FeBr_3$, $FeI_2$, $CuBr$, $CuBr_2$), and other halides, $M^1MnCl_3$, $M^1{}_2MnCl_4$, $M^1{}_2MnCl_5$, $M^1{}_2MnCl_6$, wherein $M^1$ represents a monovalent metal, and other complex halides.

The ligand constituting the complex includes, for example, OH (hydroxo), methoxy, ethoxy, propoxy, butoxy and other alkoxy groups, acetyl (OAc), propionyl and other acyl groups, methoxycarbonyl (acetato), ethoxycarbonyl and other alkoxycarbonyl groups, acetylacetonato (AA), cyclopentadienyl group, chlorine, bromine and other halogen atoms, CO, CN, oxygen atom, $H_2O$ (aquo), phosphine (e.g., triphenylphosphine and other triarylphosphine) and other phosphorus compounds, $NH_3$ (ammine), NO, $NO_2$ (nitro), $NO_3$ (nitrato), ethylenediamine, di-ethylenetriamine, pyridine, phenanthroline and other nitrogen-containing compounds. In the complexes or complex salts, the same or different ligands may be coordinated singly or in combination. Preferred ligand comprises, for example, OH, an alkoxy group, an acyl group, an alkoxycarbonyl group, acetylacetonato, a halogen atom, CO, CN, $H_2O$ (aquo), triphenylphosphine or other phosphorus compounds, or a nitrogen-containing compound inclusive of $NH_3$, $NO_2$ and $NO_3$.

Preferred complex comprises a complex contaning the preferred transition metal element. The transition metal element and the ligand may optionally be employed in combination to form a complex. Such a complex includes, for instance, acetylacetonato complexes [e.g., acetylacetonato complex of Ce, Sm, Ti, Zr, V, Cr, Mo, Mn, Fe, Ru, Co, Ni, Cu or Zn, titanylacetylacetonato complex $TiO(AA)_2$, zirconylacetylacetonato complex $ZrO(AA)_2$, vanadylacetylacetonato complex $VO(AA)_2$], carbonyl complexes or cyclopentadienyl complexes [e.g., tricarbonylcyclopentadienylmanganese(I), biscyclopentadienylmanganese(II), biscyclopentadienyliron (II), $Fe(CO)_5$, $Fe_2(CO)_9$, $Fe_3(CO)_{12}$], nitrosyl compounds [e.g., $Fe(NO)_4$, $Fe(CO)_2(NO)_2$], thiocyanato complexes [e.g., thiocyanatocobalt, thiocyanatomanganese, thiocyanatoiron], or acetyl complexes [e.g. cobalt acetate, manganese acetate, iron acetate, copper acetate, zirconyl acetate $ZrO(OAc)_2$, titanyl acetate $TiO(OAc)_2$, vanadyl acetate $VO(OAc)_2$].

As the polyacid salt, the polyacid salt available for the strong acid can be employed. Specifically, the use of these polyacid salts and a strong salt excepting the polyacid, co-existentially, accelerates the oxidation reaction of the substrate.

The catalyst comprising the imide compound shown by the formula (1) and the strong acid, or the imide compound, the strong acid and the co-catalyst, may be whichever of a homogeneous system or a heterogeneous system. The catalyst may be a solid catalyst comprising a catalytic component supported on a support or carrier, as well. As the support, use can be practically made of activated carbon, zeolite, silica, silica-alumina, bentonite, or other porous supports. In the solid catalyst, a supporting amount of the imide compound of the formula (1) may be about 0.1 to 50 parts by weight, preferably about 0.5 to 30 parts by weight and more preferably about 1 to 20 parts by weight relative to 100 parts by weight of the support. A supporting amount of the co-catalyst is about 0.1 to 30 parts by weight, preferably about 0.5 to 25 parts by weight, and more preferably about 1 to 20 parts by weight, relative to 100 parts by weight of the support.

A amount of the co-catalyst (the co-oxidizing agent) can be suitably selected from the range not deteriorating the reactivity and selectivity. The range is, for example, about 0.0001 mole (0.1 mole %) to 1 mole (100 mole %), preferably about 0.0001 to 0.7 mole, more preferably about 0.001 to 0.5 mole, and in most cases, about 0.0005 to 0.5 mole (e.g., about 0.005 to 0.5 mole).

The activities of the imide compound sometimes deteriorate as the amount of the co-catalyst increases. Therefore, in order to maintain the high activity of the oxidation catalytic system, ratio of the co-catalyst may be preferably not less than effective amount and about 0.1 mole or less, such as about 0.001 to 0.1 mole, more preferably about 0.005 to 0.08 mole, most preferably about 0.01 to 0.07 mole relative to 1 mole of the imide compound.

When a hydrogen halide or a hydroxy acid is employed as a strong acid, the co-catalyst is particularly useful as it remarkably enhances the oxidizing activity. When a heteropolyacid is employed as a strong acid, the oxygenation can be achieved with maintaining the oxidizing activity even in the absence of the co-catalyst.

Incidentally, the use of a compound, as the co-catalyst, containing at least one element selected from group 4A elements (e.g., Ti, Zr), Group 6A elements (e.g., Cr, Mo) and Group 7A elements (e.g., Mn) of the Periodic Table of Elements considerably inhibits inactivation (deactivation) of the catalyst (in particular the imide compound) even in severe reaction conditions. Therefore, the process insures oxidation of the substrate with oxygen or air with commercial advantages.

Further, the use of a compound containing the Group 4A element (e.g., Ti, Zr), Group 5A element (e.g., V), Group 6A element (e.g., Cr, Mo), Group 7A element (e.g., Mn) or Group 8 element (e.g., Fe, Co) of the Periodic Table of Elements as the co-catalyst results in remarkable enhancement of the oxidizing activity and provides effective oxidation of the substrate. By way of an example, a catalytic system comprising, as the co-catalyst, a compound containing the Group 5A element (e.g., V), Group 7A element (e.g., Mn) or Group 8 element (e.g., Co) of the Periodic Table of Elements has high activities. A catalytic system comprising, as the co-catalyst, a compound containing the Group 7A element (e.g., Mn) or Group 8 element (e.g., Fe) of the Periodic Table of Elements has high activities for the substrate and provides a ketone with high selectivity. Specifically, the use of a compound containing Group 5A elements (e.g., V) as a co-catalyst can efficiently oxygenate a methyl group or a methylene group of a substrate, and can hydroxylate a methylidine group depending on a condition.

Furthermore, the use of a compound containing an element selected from Group 4A elements, Group 5A elements, Group 6A elements, Group 7A elements and Group 8 elements of the Periodic Table of Elements, in particular a compound containing Group 5A elements of the Periodic Table of Elements (e.g., V), as a catalyst can provide a ketone, especially adamantanone or 1-hydroxyadamantanone, from adamantane component with high selectivity and in high yield even in the mild or moderate conditions.

[Substrate]

Species of substrates is not particularly restricted, and broad range of a saturated or unsaturated compound such as a hydrocarbon (e.g., an aliphatic hydrocarbon, an alicyclic hydrocarbon, an aromatic hydrocarbon), a heterocyclic compound, an aldehyde, a ketone, a carboxylic acid or derivative thereof, an alcohol, an ether and the like may be employed.

Preferred substrate comprises, for example, (a) a compound having a methyl group or a methylene group at the adjacent site of an unsaturated bond, (b) a homo- or heterocyclic compound having a methylene group, (c) a compound having a methine carbon atom, (d) a compound having a methyl group or a methylene group at the adjacent site of an aromatic ring and (e) a compound having a methyl group or a methylene group at the adjacent site of a carbonyl group. In the compound (b), the methylene group constitutes a 5- or 6-membered ring, and the ring is usually a non-aromatic homo- or heterocyclic compound. (a) The compound having a methyl group or a methylene group at the adjacent site of an unsaturated bond comprises an organic compound having a double bond and/or a triple bond. Examples of such compounds include propylene, 1-butene, 2-butene, butadiene, 1-pentene, 2-pentene, isoprene, 2-methyl-2-butene, 1-hexene, 2-hexene, 1,5-hexadiene, 2,3-dimethyl-2-butene, 3-hexene, 1-heptene, 2-heptene, 1,6-heptadiene, l-octene, 2-octene, 3-octene, 1,7-octadiene, 2,6-octadiene, 1-nonene, 2-nonene, decene, decadiene, dodecadiene, dodecatriene, undecene, undecadiene and undecatriene.

(b) Examples of the heterocyclic compound having methylene group (bl) include a cycloalkane (e.g., a cycloalkane having about 3 to 30 carbon atoms such as cyclopropane, cyclobutane, cyclopentane, cyclohexane, cycloheptane, methylcyclohexane, cyclooctane, 1,2-dimethylcyclohexane, cyclononane, isopropylcyclohexane, methylcyclooctane, cyclodecane, cyclododecane, cyclotridecane, cyclotetradecane, cyclopentadecane, cyclohexadecane, cyclooctadecane, cyclononadecane), a cycloalkene (e.g., a cycloalkene having about 3 to 30 carbon atoms such as cyclopropene, cyclobutene, cyclopentene, cyclohexene, cycloheptene, 1-methyl-l-cyclohexene, cyclooctene, cyclononene, cyclodecene, cyclododecene, limonene, menthene, menthone), a cycloalkadiene (e.g., a cycloalkadiene having about 5 to 30 carbon atoms such as cyclopentadiene, cyclohexadiene, cycloheptadiene, cyclooctadiene, cyclodecadiene, cyclododecadiene), a cycloalkatriene (e.g., cyclooctatriene), cycloalkatetraene (e.g., cyclooctatetraene) andacondensedpolycyclic hydrocarbon.

(b) The heterocyclic compound having a methylene group (b2) comprises a 5- or 6-membered cyclic compound having at least one hetero atom selected from nitrogen atom, oxygen atom and sulfur atom, or a condensed heterocyclic compound which is condensed by the 5- or 6-membered cyclic compound having the hetero atom at an aromatic ring, such as dihydrofuran, tetrahydrofuran, pyran, dihydropyran, tetrahydropyran, piperidine, piperadine, pyrrolidine and xanthene, and the like.

(c) The compound having a methine carbon atom (methylidine group) comprises, for instance, a chain hydrocarbon having a tertiary carbon atom (c1), a bridged cyclic hydrocarbon (c2) and the like.

Examples of the chain hydrocarbon having a tertiary carbon atom (cl) include a aliphatic hydrocarbon having about 4 to 10 carbon atoms such as isobutane, isopentane, isohexane, 3-methylpentane, 2,3-dimethylbutane, 2-methylhexane, 3-methylhexane, 2,3-dimethylpentane, 2,4-dimethylpentane, 2,3,4-trimethylpentane, 3-ethylpentane, 2,3-dimethylhexane, 2,4-dimethylhexane, 3,4-dimethylhexane, 2,5-dimethylhexane, 2-propylhexane, 2-methylheptane, 4-methylheptane, 2-ethylheptane, 3-ethylheptane, 2,6-dimethylheptane, 2-methyloctane, 3-methyloctane, 2,7-dimethyloctane and 2-methylnonane.

The bridged cyclic hydrocarbon (c2) comprises, for example, a bridged cyclic hydrocarbon [e.g., bicyclo hydrocarbon such as decalin, hexahydroindan, carane, bornane, norbornene, norbornane, vinylnorbornene and norbornadiene; a tricyclo hydrocarbon such as homoblendane, adamantane and derivatives thereof (e.g., methyladamantane, 1,3-dimethyladamantane, ethyladamantane, chloroadamantane, adamantanol, adamantanone, methyladamantanone, dimethyladamantanone, formyladamantanone), tricyclo[4.3.1.1$^{2,5}$]undecane; and a tetracyclohydorocarbon such as tetracyclo[4.4.0.1.$^{2,5}$.1.$^{7,10}$] dodecane), a dimer of a diene or hydrogen adduct thereof (e.g., dicyclopentane, dicyclohxane, dicyclopentene, dicyclohexadiene, dicyclopentadiene) and terpene (e.g., pinane, pinene, camphor, bornene, caryophyllene).

(d) Examples of the compound having a methyl group or a methylene group at the adjacent site of an aromatic ring include an aromatic hydrocarbon having an alkyl group (e.g., toluene, o-, m- or p-xylene, 1,2,3-trimethylbenzene, 1,2,4-trimethylbenzene, 1,3,5-trimethylbenzene (mesitylene), 1,2,3,4-tetramethylbenzene, 1,2,3,5-tetramethylbenzene, 1,2,4,5-tetramethylbenzene (durene), 1,2,3,4,5,6-hexamethylbenzene, ethylbenzene, propylbenzene, cumene, o-, m- or p-ethyltoluene, butylbenzene, 1,4-diethylbenzene, 1-methylnaphthalene, 2-methylnaphthalene, 1,5-dimethylnaphthalene, 2,5-dimethylnaphthalene, 1-methylanthracene, 2-methylanthracene, 9-methylanthracene, dimethylanthracene, trimethylanthracene, 4,4'-dimethylbiphenyl, dibenzyl, diphenylmethane, triphenylmethane), an aromatic hydrocarbon having a cyclic methylene group (e.g., a condensed polycyclic aromatic hydrocarbon condesed by a about 5 to 8-membered ring, such as indane, indene, tetralin, dihydronaohthalene, fluorene, phenalene) and a heterocyclic compound having an alkyl group (e.g., a picoline such as 2-methylfuran, 3-methylfuran, 2-methylpyran, 3-methylpyran, 4-methylpyran, 3,4-dimethylpyran, 4-methylchroman, 6-methylchroman, 2-methylpyridine, 3-methylpyridine and 4-methylpyridine, a lutidine such as 2,3-dimethylpyridine, a collidine such as 2,4,6-trimethylpyridine, 2-ethylpyridine, 3-ethylpyridine, 4-ethylpyridine, methylquinoline and methylindole).

(e) The compound having a (active) methyl group or methylene group at the adjacent site of a carbonyl group comprises, for instance, an aldehyde (e1), a ketone (e2) and a carboxylic acid or dericative thereof (e3).

The aldehyde (e1) comprises, for example, an aliphatic aldehyde (e.g., an aliphatic monoaldehyde having about 2 to 12 carbon atoms such as acetaldehyde, propionaldehyde, butylaldehyde, isobutylaldehyde, pentylaldehyde, hexylaldehyde, heptylaldehyde, octylaldehyde, nonylaldehyde and decylaldehyde, an aliphatic polyaldehyde such as malonaldehyde, succinaldehyde, adipic aldehyde and sebacic aldehyde), an aromatic aldehyde (e.g., benzaldehyde, anisaldehyde) an alicyclic aldehyde (e.g., formylcyclohexane, citronellal), a bridged cyclic aldehyde (e.g., formylnorbornene) and a heterocyclic aldehyde (e.g., nicotinic aldehyde, furfural).

Examples of the ketone include an aliphatic ketone (e.g., acetone, methylethylketone, methylisopropylketone, methylisobutylketone, methyl-t-butylketone, 2-pentanone, 3-pentanone, 2-hexanone, 3-hexanone, 2-heptanone, 3-heptanone, 4-heptanone, 2-octanone, 3-octanone, 4-octanone, 2-nonanone and 2-decanone), a cyclic ketone (e.g., a non-aromatic cyclic mono- or polyketone such as cyclopentanone, cyclohexanone, methylcyclohexanone, dimethylcyclohexanone, cycloheptanone, isophorone, cyclooctanone, cyclononanone, cyclodecanone, cyclohexadione and cyclooctadione; a cyclic ketone having an aromatic ring such as α-tetralone, β-tetralone and indanone), a bridged cyclic ketone (e.g., pinocamphone, pinocarbon), an aromatic ketone (e.g., acetophenene, propiophenone) and a heterocyclic ketone (e.g., pyrrolidone, pyperidone).

The carboxylic acid or derivatives thereof (e3) comprises, for example, an aliphatic dicarboxylic acid or dericatives thereof (e.g., malonic acid or an ester thereof, succinic acid or an ester thereof and glutaric acid or an ester thereof).

These substrates may be substituted by a suitable functional group, such as a halogen atom, an oxo group, a hydroxyl group, an alkoxy group, a carboxyl group, an alkoxycarbonyl group, an acyl group, an alkyl group, an alkenyl group (e.g., an allyl group), a cycloalkyl group, an aryl group, a vinyl group, an amino group, an alkylamino group, an amido group, a nitro group, a nitrile group, an acylamino group, a mercapto group, a sulfonyl group, a sulfinyl group, a sulfide group and a phosphino group.

Further, preferred substrate comprises, for instance, a bridged cyclic hydrocarbon having about 6 to 16 carbon atoms (in particular about 7 to 14 carbon atoms), specifically a bridged cyclic hydrocarbon such as adamantane or derivatives thereof (e.g., adamantanol) and a compound having a methyl group or a methylene group at a benzyl site.

Contacting the substrate with oxygen in the presence of the catalyst, a methyl group, a methylene group or a hydroxymethylene group is selectively oxygenated. Especially, a carbon site of the methylene group adjacent to a methine group or an aromatic ring is selectively oxidized even in a mild or moderate condition, and, depending on a reaction condition, a carbon site of the methine group can be hydroxylated to efficiently generate a corresponding chain or cyclic ketone (e.g., a monoketone, a polyketone, a hydroxyketone).

[Oxygenation reaction]

The oxygen used in oxygenation of the substrate may be active oxygen, but molecular oxygen is practically employed for economical advantages. Such molecular oxygen is not specifically limited, and use may be made of whichever of pure oxygen, or oxygen diluted with an inert gas such as nitrogen, helium, argon or carbon dioxide gas. Air is preferably employed from the viewpoints of not only handling property and safety, but also economical property.

An amount of oxygen can be selected from a range according to the species of the substrate, and usually is, 0.5 mole or more (e.g., 1 mole or more), preferably about 1 to 100 moles, and more preferably about 2 to 50 moles relative to 1 mole of the substrate. The oxygen is practically used in an excess mole relative to the substrate. In specific, the reaction is advantageously carried out in an atmosphere containing molecular oxygen such as air or oxygen gas.

Oxygenation process of the present invention is usually conducted in an inert organic solvent. As the organic solvents, there may be mentioned, for example, acetic acid, propionic acid and other organic acids, acetonitrile, propionitrile, benzonitrile and other nitriles, formamide, acetamide, dimethylformamide (DMF), dimethylacetamide and other amides, hexane, octane and other aliphatic hydrocarbons, benzene, toluene and other aromatic hydrocarbons, chloroform, dichloromethane, dichloroethane, carbon tetrachloride, chlorobenzene and other halogenated hydrocarbons, nitrobenzene, nitromethane, nitroethane and other nitro compounds, ethyl acetate, butyl acetate and other esters, and mixtures of these solvents. Incidentally, the substrate may be optionally employed as the reaction solvent, if used in an excess amount. Use may practically be made of, as the solvent, acetic acid or other organic acids, acetonitrile, benzonitrile or other nitrites.

A reaction temperature can be voluntarily selected according to the species of the substrate. The temperature is, for instance, about 0 to 300° C., preferably about 30 to 250° C., more preferably about 40 to 200w C, and practically about 50 to 150° C. The present invention have a feature that the oxygenation reaction is smoothly proceeded when the reaction is conducted in the relatively high temperature condition.

A pH of the liquid phase of the reaction system is about 0.01 to 3, preferably about 0.1 to 3. Such adjustment of the pH of the liquid phase of the reaction system proceeds the oxygenation, more selectively, and provides a ketone with high selectivity.

The reaction may be carried out at ambient pressure (atmospheric pressure) or under a pressure (under a load). When the reaction is conducted under a pressure, the pressure is, usually, about 1 to 100 atm (e.g., about 1.5 to 80 atm), preferably about 2 to 70 atm, and more preferably about 5 to 50 atm. A reaction time can be liberally chosen within a range of about 30 minutes to 48 hours, preferably about 1 to 36 hours, and more preferably about 2 to 24 hours, according to the reaction temperature and pressure. Especially, in the case that adamantane is oxygenated, the reaction of relatively long time (e.g., about 5 to 48 hours, preferably about 5 to 36 hours, and more preferably about 6 to 30 hours) preferentially produces a ketone such as adamantanone, 1-hydroxy-adamantanone or a polyketone, easily, with inhibiting the generation of an alcohol such as adamantanol or adamantane polyol.

The process of the present invention is useful for oxygenating the substrate to obtain an oxo compound corresponding to the substrate, efficiently. The process provides a ketone with high conversion and selectivity even in a mild or moderate condition. Specifically, a methylene group of the substrate may be oxygenated by one step.

The reaction may be effected, in the presence of the catalyst, by contacting the substrate with oxygen, and may be effected in a conventional manner such as in a batch system, semi-batch system or continuous system, in the presence of molecular oxygen or under flow of molecular oxygen. After completion of the reaction, a reaction product can easily be isolated and purified according to a conventional technology, such as filtration, condensation, distillation, extraction, crystallization, recrystallization, column chromatography, or other isolation means, or a combination of these technologies.

INDUSTRIAL APPLICABILITY OF THE INVENTION

In the process of the present invention, a ketone which can be used as an intermediate product of a medicine, a perfume, a dye, a food and an intermediate in an organic synthesis, from a substrate.

The process of the present invention can effectively oxygenate a substrate since the imide compound shown by formula (1) and a strong acid, or the imide compound, the strong acid and a co-catalyst and oxygen are combined. Moreover, the substrate can be oxygenate even in a miled or moderate condition to provide a ketone with high conversion and selectivity.

The following examples are intended to describe this invention in further detail and should by no means be interpreted as defining the scope of the invention.

EXAMPLES

Example 1

To 25 ml of acetic acid were added 10 mmol of adamantane, 1 mmol of N-hydroxyphthalimide, 0.05 mmol of 98% by weight sulfuric acid and 0.05 mmol of acetylacetonatovanadium V(AA)$_3$, and the resultant mixture (pH 1.7) was stirred under an oxygen atmosphere at a temperature of 75° C. for 6 hours. The products in the reaction mixture were analyzed by gas chromatography, and, as a result, adamantane was converted into adamantanone (yield 25%) and 1-hydroxyadamantanone (yield 29%) with a conversion of 96%. Incidentally, excepting the above, 1-adamantanol (yield 10%), 1,3-adamantanediol (yield 12%) and other products (polyketone such as adamantanedione) (yield 20%) were formed.

Example 2

The reaction was conducted in the same manner as Example 1 except that the proportion of 98% by weight of sulfuric acid was 0.5 mmol (thus, pH of the mixture is 0.8), and, as a result, adamantane was converted into adamantanone (yield 36%) and 1-hydroxyadamantanone (yield 38%) with a conversion of 97%. Incidentally, excepting the above, 1-adamantanol (yield 3%), 1,3-adamantanediol (yield 4%) and other products (polyketone such as adamantanedione) (yield 16%) were formed.

Example 3

The reaction was conducted in the same manner as Example 2 except that the reaction was conducted by stirring at a temperature of 85° C. for 8 hours, the pH of the mixture was 0.3, and as a result, adamantane was converted into adamantanone (yield 31%) and 1-hydroxyadamantanone (yield 30%) with a conversion of 95%. Incidentally, excepting the above, 1-adamantanol (yield 1%), 1,3-adamantanediol (yield 3%) and other products (polyketone such as adamantanedione) (yield 30%) were formed.

Example 4

The reaction was conducted in the same manner as Example 2 except using hydrogen bromide instead of 98% by weight of sulfuric acid, the pH of the mixture was 0.9, and as a result, adamantane was converted into adamantanone (yield 26%) and 1-hydroxyadamantanone (yield 22%) with a conversion of 92%. Incidentally, excepting the above, 1-adamantanol (yield 16%), 1,3-adamantanediol (yield 16%) and other products (polyketone such as adamantanedione) (yield 12%) were formed.

Example 5

To 25 ml of acetic acid were added 10 mmol of adamantane, 1 mmol of N-hydroxyphthalimide and 0.2 mmol of phosphovanadotungstic acid ($PV_4W_8O_{40} \cdot 30H_2$), and the resultant mixture (pH 1.9) was stirred under an oxygen atmosphere at a temperature of 75° C. for 6 hours. The products in the reaction mixture were analyzed by gas chromatography, and, as a result, adamantane was converted into adamantanone (yield 32%) and 1-hydroxyadamantanone (yield 16%) with a conversion of 79%. Incidentally, excepting the above, 1-adamantanol (yield 15%), 1,3-adamantanediol (yield 8%) and other products (polyketone such as adamantanedione) (yield 8%) were formed.

Example 6

To 25 ml of acetic acid were added 10 mmol of adamantane, 1 mmol of N-hydroxyphthalimide and 0.3 mmol of phosphovanadomoribdic acid ($PV_5Mo_7O_{40} \cdot 30H_2$), and the resultant mixture (pH 1.2) was stirred under an oxygen atmosphere at a temperature of 75° C. for 6 hours. The products in the reaction mixture were analyzed by gas chromatography, and, as a result, adamantane was converted into adamantanone (yield 30%) and 1-hydroxyadamantanone (yield 15%) with a conversion of 77%. Incidentally, excepting the above, 1-adamantanol (yield 16%), 1,3-adamantanediol (yield 8%) and other products (polyketone such as adamantanedione) (yield 8%) were formed.

Example 7

The reaction was conducted in the same manner as Example 6 except that the proportion of phosphovanadomoribdic acid ($PV_5Mo_7O_{40} \cdot 30H_2$) was 0.05 mmol, the pH of the mixture was 2.7, and, as a result, adamantane was converted into adamantanone (yield 34%) and 1-hydroxyadamantanone (yield 13%) with a conversion of 78%. Incidentally, excepting the above, 1-adamantanol (yield 18%), 1,3-adamantanediol (yield 5%) and other products (polyketone such as adamantanedione) (yield 8%) were formed.

Example 8

The reaction was conducted in the same manner as Example 6 except that the proportion of phosphovanadomoribdic acid ($PV_2Mo_{10}O_{40} \cdot 30H_2$) was 0.1 mmol, the pH of the mixture was 2.2, and, as a result, adamantane was converted into adamantanone (yield 31%) and 1-hydroxyadamantanone (yield 11%) with a conversion of 65%. Incidentally, excepting the above, 1-adamantanol (yield 15%), 1,3-adamantanediol (yield 3%) and other products (polyketone such as adamantanedione) (yield 5%) were formed.

COMPARATIVE EXAMPLE 1

The reaction was conduced in the same manner as Example 1 without using 98% by weight of sulfuric acid, the pH of the mixture was 4.6, and, as a result adamantane was converted into adamantanone (yield 7%) and 1-hydroxyadamantanone (yield 1%) with a conversion of 99%. Incidentally, excepting the above, 1-adamantanol (yield 28%), 1,3-adamantanediol (yield 35%) and other products (polyol such as adamantanetriol) (yield 28%) were formed.

COMPARATIVE EXAMPLE 2

The reaction was conducted in the same manner as Example 1 except using 1 mmol of oxalic acid instead of 98% by weight of sulfuric acid, the pH of the mixture was 3.7, and, as a result, adamantane was converted into adamantanone (yield 8%) and 1-hydroxyadamantanone (yield 2%) with a conversion of 99%. Incidentally, excepting the above, 1-adamantanol (yield 26%), 1,3-adamantanediol (yield 33%) and other products (polyol such as adamantanetriol) (yield 30%) were formed.

COMPARATIVE EXAMPLE 3

The reaction was conducted in the same manner as Example 6 except using the phosphovanadomoribdic acid ($PV_2Mo_{10}O_{40} \cdot 30H_2$) treated with alkali to be pH7, the pH of the mixture was 4.4, and, as a result, adamantane was converted into adamantanone (yield 6%) and 1-hydroxyadamantanone (yield 1%) with a conversion of 89%. Incidentally, excepting the above, 1-adamantanol (yield 42%), 1,3-adamantanediol (yield 27%) and other products (polyol such as adamantanetriol) (yield 13%) were formed.

COMPARATIVE EXAMPLE 4

The reaction was conducted in the same manner as Example 1 without using N-hydroxyphthalimide, the pH of the mixture was 0.1, and, as a result, the reaction was scarcely exceeded.

Obvious from the above Examples, in the present invention, adamantane is efficiently oxygenated to produce a corresponding ketone, efficiently.

What is claimed is:

1. A catalyst composition for oxygenating a bridged cyclic hydrocarbon with oxygen, which comprises;

an imide compound shown by the following formula (1)

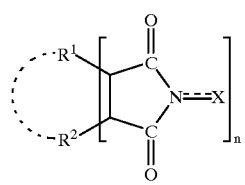

(1)

wherein $R^1$ and $R^2$ independently represent a hydrogen atom, a halogen atom, an alkyl group, an aryl group, a cycloalkyl group, a hydroxyl group, an alkoxy group, a carboxyl group, an alkoxycarbonyl group, or an acyl group, or $R^1$ and $R^2$ may bond together to form a double bond or an aromatic or non-aromatic ring; X represents an oxygen atom or a hydroxyl group; and n denotes an integer of 1 to 3, and a strong acid selected from the group consisting of a hydrogen halide, a hydrohalogenic acid, sulfuric acid and a polyacid.

2. A catalyst composition according to claim 1, wherein $R^1$ and $R^2$, in said imide compound shown by the formula (1), bond together to form an aromatic or a non-aromatic 5 to 12 membered ring.

3. A catalyst composition according to claim 1, wherein $R^1$ and $R^2$, in said imide compound shown by the formula (1), bond together to form a cycloalkane ring which may have a substituent, a cycloalkene ring which may have a substituent, a bridged hydrocarbon ring which may have a substituent and an aromatic ring which may have a substituent.

4. A catalyst composition according to claim 1, wherein said imide compound shown by the formula (1) is a compound shown by the following formulas (1a), (1b), (1c), (1d), (1e) and (1f);

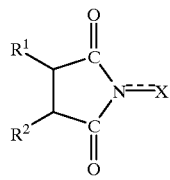
(1a)

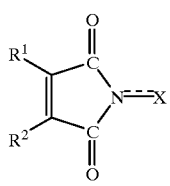
(1b)

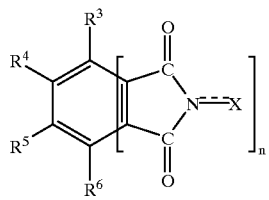
(1c)

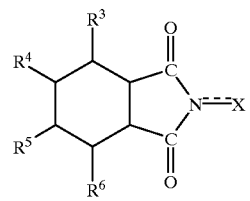
(1d)

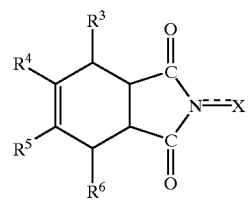
(1e)

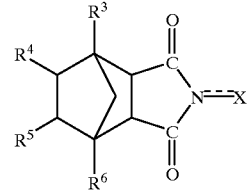
(1f)

wherein $R^3$, $R^4$, $R^5$ and $R^6$ are the same or different a hydrogen atom, an alkyl group, a hydroxyl group, an alkoxy group, a carboxyl group, an alkoxycarbonyl group, an acyl group, a nitro group, a cyano group, an amino group or a halogen atom; and $R^1$, $R^2$ and n have the same meanings as defined above.

5. A catalyst according to claim 1, wherein said imide compound shown by the formula (1) is at least one compound selected from the group consisting of N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxyhetimide, N-hydroxyhimimide, N-hydroxytrimellitimide, N,N'-dihydroxypyromellitimide and N,N'-dihydroxynaphthalenetetracarboximide.

6. A catalyst composition according to claim 1, wherein a pKa value of said strong acid at 25° C. is in a range of −15 to 2.

7. A catalyst composition according to claim 1, which comprises said imide compound shown by the formula (1), said strong acid and a co-catalyst.

8. A catalyst composition according to claim 7, wherein said co-catalyst is a compound containing at least one element selected from the group consisting of Group 2A elements of the Periodic Table of Elements, transition metal elements and Group 3B elements of the Periodic Table of Elements.

9. A catalyst composition according to claim 7, wherein said co-catalyst is a compound containing at least one element selected from the group consisting of Group 3A elements, Group 4A elements, Group 5A elements, Group 6A elements, Group 7A elements, Group 8 elements, Group 1B elements and Group 2B elements of the Periodic Table of Elements.

10. An oxygenation process comprises contacting a bridged cyclic hydrocarbon with oxygen in the presence of the catalyst composition claimed in claim 1.

11. A oxygenation process according to claim 10, said bridged cyclic hydrocarbon is an adamantane or derivative thereof.

12. A process for producing a ketone comprising contacting a bridged cyclic hydrocarbon with oxygen at pH 0.01 to 3 in the presence of a catalyst composition recited in claim 1 or 7.

13. A catalyst composition according to claim 1, wherein the strong acid is 0.001 to 100 mole % relative to 1 mole of the bridged cyclic hydrocarbon.

14. A catalyst composition according to claim 1, wherein the strong acid is 0.1 to 50 mole % relative to 1 mole of the bridged cyclic hydrocarbon.

15. A catalyst composition according to claim 1, further comprising oxygen.

16. A catalyst composition for oxygenating a bridged cyclic hydrocarbon with oxygen, which comprises;

an imide compound shown by the following formula (1)

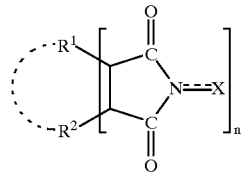
(1)

wherein $R^1$ and $R^2$ independently represent a hydrogen atom, a halogen atom, an alkyl group, an aryl group, a cycloalkyl group, a hydroxyl group, an alkoxy group, a carboxyl group, an alkoxycarbonyl group, or an acyl group, or $R^1$ and $R^2$ may bond together to form a double bond or an aromatic or non-aromatic ring; X represents an oxygen atom or a hydroxyl group; and n denotes an integer of 1 to 3, and a strong acid selected from the group consisting of a hydrogen halide, a hydrohalogenic acid, oxygen acid and a super strong acid.

* * * * *